(12) United States Patent
Guo et al.

(10) Patent No.: US 12,195,785 B2
(45) Date of Patent: Jan. 14, 2025

(54) GENE TARGET REGION ENRICHMENT METHOD AND KIT

(71) Applicant: SHANGHAI ZENISIGHT LTD., Shanghai (CN)

(72) Inventors: Zhiwei Guo, Shanghai (CN); Yinghui Li, Shanghai (CN); Qian Chen, Shanghai (CN); Rongjun Hu, Shanghai (CN)

(73) Assignee: SHANGHAI ZENISIGHT LTD., Shanghai (CN)

( * ) Notice: Subject to any disclaimer, the term of this patent is extended or adjusted under 35 U.S.C. 154(b) by 619 days.

(21) Appl. No.: 17/419,540

(22) PCT Filed: Dec. 9, 2019

(86) PCT No.: PCT/CN2019/123891
§ 371 (c)(1),
(2) Date: Jun. 29, 2021

(87) PCT Pub. No.: WO2020/140693
PCT Pub. Date: Jul. 9, 2020

(65) Prior Publication Data
US 2023/0159984 A1    May 25, 2023

(30) Foreign Application Priority Data

Jan. 2, 2019   (CN) .......................... 201910002408.5
Sep. 20, 2019  (CN) .......................... 201910897689.5

(51) Int. Cl.
C12Q 1/68      (2018.01)
C12Q 1/6806    (2018.01)
C12Q 1/6853    (2018.01)

(52) U.S. Cl.
CPC ......... *C12Q 1/6806* (2013.01); *C12Q 1/6853* (2013.01)

(58) Field of Classification Search
None
See application file for complete search history.

(56) References Cited

U.S. PATENT DOCUMENTS

| 7,914,995 | B2 | 3/2011 | Liu et al. | |
|---|---|---|---|---|
| 2013/0149695 | A1 | 6/2013 | Lee et al. | |
| 2014/0051595 | A1* | 2/2014 | So ....................... | C12Q 1/6876 435/6.12 |
| 2014/0329245 | A1 | 11/2014 | Spier et al. | |
| 2016/0203259 | A1* | 7/2016 | Scolnick ............. | C12Q 1/6886 506/2 |
| 2017/0335369 | A1* | 11/2017 | Fields ................... | C12Q 1/6806 |
| 2018/0163251 | A1* | 6/2018 | Guo ........................ | C12P 19/34 |

FOREIGN PATENT DOCUMENTS

| CN | 107922970 A | 4/2018 |
|---|---|---|
| CN | 108251502 A | 7/2018 |
| JP | 2003-38180 A | 2/2003 |
| JP | 2017-537657 A | 12/2017 |
| JP | 2018-521675 A | 8/2018 |
| WO | 2018028001 A1 | 2/2018 |
| WO | 2021/051665 A1 | 3/2021 |

OTHER PUBLICATIONS

Office Action issued for JP patent application Serial No. 2021-538411, dated Aug. 2, 2022, with English translation.
Decision to Grant a Patent issued for JP patent application Serial No. 2021-538411, dated Dec. 2, 2022, with English translation.
Dapprich, J. et al. "The Next Generation of Target Capture Technologies-large DNA Fragment Enrichment and Sequencing Determines Regional Genomic Variation of High Complexity" BMC Genomics, vol. 7, Jul. 9, 2016 (Jul. 9, 2016), the abstract, and figure 1.
International Search Report issued for PCT/CN2019/123891, dated Mar. 6, 2020.
Written Opinion of the International Searching Authority issued for PCT/CN2019/123891, dated Mar. 6, 2020.
Beltz, K. et al. "A High-Performing and Cost-Effective SNP Genotyping Method Using rhPCR and Universal Reporters" Advances in Bioscience and Biotechnology (2018) 9, 497-512.
Gansauge, M-T. et al. "Single-stranded DNA library preparation from highly degraded DNA using T4 DNA ligase" Nucleic Acids Res. (2017) 45(10).
Paruzynski, A. et al. "Genome-wide high-throughput integrome analyses by nrLAM-PCR and next-generation sequencing" Nat Protoc. (2010), 5(8), 1379-95.
Office Action issued for JP patent application Serial No. 2021-538411, dated Jan. 4, 2022, with English machine translation.
Extended European Search Report issued for EP patent application Serial No. 19907784.3, dated Aug. 18, 2022.
Office Action issued for CN patent application Serial No. 201910897689.5, dated Jan. 27, 2021, with English machine translation.

* cited by examiner

*Primary Examiner* — Suryaprabha Chunduru
(74) *Attorney, Agent, or Firm* — WESTMAN, CHAMPLIN & KOEHLER, P.A.; Amanda M. Prose

(57) ABSTRACT

Provided is a gene target region enrichment method and a kit. The method comprises (1) amplifying fragmented DNA comprising a target region by means of a specific probe so as to obtain a captured-extension product, wherein the specific probe comprises a sequence complementary to the target region of the fragmented DNA, and the 3' terminal nucleotide of the specific probe is modified to prevent a ligation reaction at the 3' terminal of the specific probe; and (2) linking the 3' terminal of the captured-extension product obtained in step (1) to linker DNA to obtain a ligation product.

1 Claim, 2 Drawing Sheets
Specification includes a Sequence Listing.

| Universal sequence for probe sequencing (P1) | Complementary sequence with probe | Sequence of target region | sequence of linker | molecular tag | sample tag | universal sequence for linker sequencing (A) |
|---|---|---|---|---|---|---|

| AF sequence | Exon sequence of EGFR gene 21 | AR sequence |

SEQUENCE LISTING

```
<160> NUMBER OF SEQ ID NOS: 30

<210> SEQ ID NO 1
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 1
ccgctttcct ctctatgggc agtcggtgat cctggcagcc aggaacgtac tggtgaa      57
```

<210> SEQ ID NO 2
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 2
ccgctttcct ctctatgggc agtcggtgat cctggcagcc aggaacgtac tggtgaa    57

<210> SEQ ID NO 3
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 3
ccgctttcct ctctatgggc agtcggtgat cctggcagcc aggaacgtac tggtgaa    57

<210> SEQ ID NO 4
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 4
ccgctttcct ctctatgggc agtcggtgat cctggcagcc aggaacgtac tggtgaa    57

<210> SEQ ID NO 5
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 5
ccgctttcct ctctatgggc agtcggtgat cctggcagcc aggaacgtac tggtgaa    57

<210> SEQ ID NO 6
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 6
ccgctttcct ctctatgggc agtcggtgat cctggcagcc aggaacgtac tggtgaa    57

<210> SEQ ID NO 7
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 7
ccgctttcct ctctatgggc agtcggtgat cctggcagcc aggaacgtac tggtgat    57

<210> SEQ ID NO 8
<211> LENGTH: 58
<212> TYPE: DNA
<213> ORGANISM: Artificial Sequence
<220> FEATURE:

```
<223> OTHER INFORMATION: Synthetic oligonucleotide

<400> SEQUENCE: 8
ccgctttcct ctctatgggc agtcggtgat cctggcagcc aggaacgtac tgrgtgat      58

<210> SEQ ID NO 9
<211> LENGTH: 51
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(12)
<223> OTHER INFORMATION: n is a, c, g, or t

<400> SEQUENCE: 9
ggatccnnnn nncagcttgg actgagtcgg agacacgcag ggatgagatg g             51

<210> SEQ ID NO 10
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(12)
<223> OTHER INFORMATION: n is a, c, g, or t

<400> SEQUENCE: 10
ggatccnnnn nngttctcct tactgagtcg gagacacgca gggatgagat gg            52

<210> SEQ ID NO 11
<211> LENGTH: 51
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(12)
<223> OTHER INFORMATION: n is a, c, g, or t

<400> SEQUENCE: 11
ggatccnnnn nnttacctta gctgagtcgg agacacgcag ggatgagatg g             51

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 12
gatcacagat tttgggc                                                   17

<210> SEQ ID NO 13
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 13
tttgcctcct tctgc                                                     15
```

```
<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 14
aactgctggg tgcgga                                                      16

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
gtctcagcct ctctatgggc agtcggtgat                                       30

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
ccatctcatc cctgcgtgtc tccgactcag                                       30

<210> SEQ ID NO 17
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 17
ccgctttcct ctctatgggc agtcggtgat tagttggatg ggattattt                  49

<210> SEQ ID NO 18
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 18
ccgctttcct ctctatgggc agtcggtgat ttttttttgg gagtttaaat aaagatta        58

<210> SEQ ID NO 19
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 19
ccgctttcct ctctatgggc agtcggtgat tttaaaatag agttagtttt agttttt          57

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 20
ttccaggagg cacagaaatt ac                                        22

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
cttccgacga ggtcgatact                                           20

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
catgcacaga gagaaatacc cgaat                                     25

<210> SEQ ID NO 23
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 23
cagattttgg gcg                                                  13

<210> SEQ ID NO 24
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 24
gcgtgatgag t                                                    11

<210> SEQ ID NO 25
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 25
gcgtggacaa cccccac                                              17

<210> SEQ ID NO 26
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 26
cacggtggag gtgaggc                                              17

<210> SEQ ID NO 27
<211> LENGTH: 17
```

```
<212> TYPE: DNA
<213> ORGANISM: Artificial Sequence
<220> FEATURE:
<223> OTHER INFORMATION: Synthetic oligonucleotide

<400> SEQUENCE: 27
ccatctcatc cctgcgt                                                  17

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
tccgactcag taaggagaac ga                                            22

<210> SEQ ID NO 29
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 29
ccgctttcct ctctatgggc agtcggtgat ccaatattgt ctttgtgttc ccggacatag   60
tcct                                                                64

<210> SEQ ID NO 30
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 30
ccgctttcct ctctatgggc agtcggtgat ctatggccat tcttccagga ggcacagaaa   60
ttact                                                               65
```

GENE TARGET REGION ENRICHMENT METHOD AND KIT

CROSS-REFERENCE TO RELATED APPLICATION

This Application is a Section 371 National Stage Application of International Application No. PCT/CN2019/123891, filed Dec. 9, 2019 and published as WO2020/140693 A1 on Jun. 9, 2020, in Chinese, which claims priority to Chinese patent application serial no. 201910002408.5, filed Jan. 2, 2019, and Chinese patent application serial no. 201910897689.5, filed Sep. 20, 2019, the contents of which are hereby incorporated by reference in their entirety.

TECHNICAL FIELD

The present invention relates to the field of biotechnology, in particular, to a gene target region enrichment method and kit.

BACKGROUND OF THE INVENTION

Gene sequencing technology has gone through nearly half a century since it appears in the 1970s. The emergence of PCR technology in 1985 has promoted the development of the entire field of molecular biology. Next-generation sequencing technology (NGS) has the advantages of accuracy, sensitivity, and high throughput. As the cost of sequencing continues to decrease, its application range continues to expand, but its application is also subject to diverse requirement and time-consuming laborious library construction. In the process of building clinical samples such as plasma samples, the existing forms of DNA are usually short fragments, damaged, single-stranded or partially double-stranded. For these existing forms, especially DNA with fragments less than 200 bp, the present PCR technology cannot achieve good capture and enrichment.

For the enrichment of tiny DNA fragments, the existing technology still mainly uses the traditional PCR library construction method or the method of first adding a linker and then amplifying, such as the hybrid capture method. However, for the former, due to the need for double-ended primers, the length of fragments suitable for amplification is greatly limited, and the preference in amplification results in high heterogeneity of the product, and errors accumulated by exponential amplification leads to subsequent sequencing result is inaccurate. While for the latter, although the requirement for the length of the enriched fragment is not as strict as PCR, the ligation reaction needs to be performed firstly, and the efficiency of ligation is usually only 20% to 50%, resulting in low capture efficiency, in addition, there is also the problem of being easy to lose rare molecules due to difficulty in ligation. Recently developed technologies in order to solve the problem of NGS library construction include such as molecular inversion probes, Multiple PCR and the like. Compared with hybrid capture technology, the molecular inverted probe has better specificity, but design of its pocket-shaped probe is complicated, and it is not suitable for the enrichment of tiny DNA fragments. Multiple PCR technology is suitable for large-scale samples and is the most widely used. But neither of them is suitable for enrichment of small DNA fragments at low starting concentration, since either the primer design requirements are extremely high and the homogeneity of the amplicon is poor, or the homogeneity of the amplified product is good but the requirement to the concentration of the starting sample is very high. These prior arts usually require double-ended primers to construct libraries, so, in order to remove linker dimer contamination, a purification step must be introduced, which results in the loss of information in small fragments of double-stranded DNA, damaged double-stranded DNA, and single-stranded DNA molecules. However, in some genomic regions where transcription is active, it is precisely these forms of DNA. To sum up, the prior arts cannot satisfy the demand for enrichment of fragmented, especially tiny DNA of 200 bp or less. Therefore, the main technical purpose of the present invention is to provide a method for efficient enrichment of the target regions in fragmented DNA, breaking the bottleneck of the low ligation efficiency limiting the enrichment efficiency, inhibiting the production of unintended ligation products and increasing the capture efficiency of rare molecules with the target regions while maintaining the uniformity of the product.

SUMMARY OF THE INVENTION

In view of the above-mentioned shortcomings of the prior art, the object of the present invention is to provide a gene target region enrichment method for solving the problems in the prior art.

To achieve the above objectives and other related objectives, the present invention provides a gene target region enrichment method, including:

comprising:

(1) amplifying fragmented DNA comprising the target region(s) via specific probes to provide captured-extension products, wherein the specific probe comprises a sequence complementary to the target region of the fragmented DNA, and the 3' terminal nucleotide of the specific probe is modified to prevent a ligation reaction at the 3' terminal of the specific probe;

(2) linking the 3' end of the captured-extension product obtained in step (1) to linker DNA to obtain a ligation product.

Another aspect of the present invention provides a kit for enriching a fragmented DNA target region, which includes a specific probe and linker DNA (sometimes called "adapter DNA") suitable for the gene target region enrichment method.

DETAILED DESCRIPTION OF THE EMBODIMENTS

Figures 1, 2:
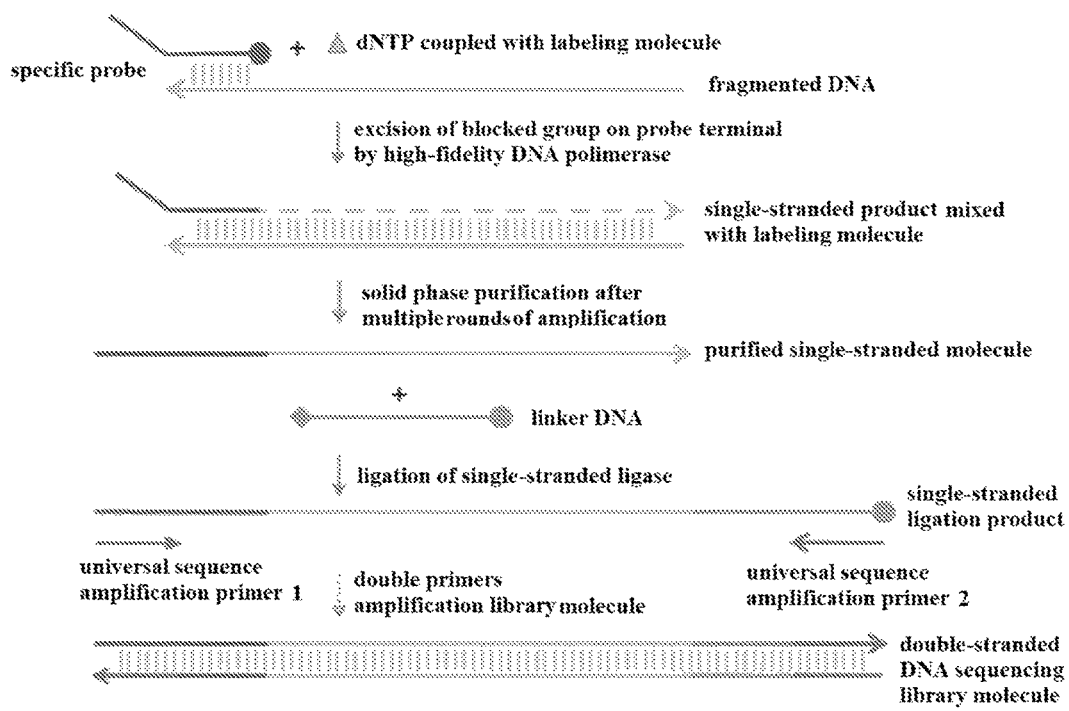
FIG. 1 is a schematic flowchart of an enrichment process for a target region in an embodiment of the present invention.
FIG. 2 is a schematic diagram of a library molecule constructed according to an embodiment of the present invention.

The inventors of the present invention have provided a gene target region enrichment method after a lot of exploratory research. The gene target region enrichment method is simple to operate and has reliable results, especially for short-length nucleotide. Based on this, the present invention has been completed.

The first aspect of the present invention provides a gene target region enrichment method, including:

(1) amplifying fragmented DNA comprising the target region(s) via specific probes to provide captured-extension products, wherein the specific probe comprises a sequence complementary to the target region of the fragmented DNA, and the 3' terminal nucleotide of the specific probe is modified to prevent a ligation reaction at the 3' terminal of the specific probe;

(2) linking the 3' end of the captured-extension product obtained in step (1) to linker DNA to obtain a ligation product.

The gene target region enrichment method provided by the present invention may include: amplifying the fragmented DNA including the target region by a specific probe to provide a captured-extension product. During the reaction, the specific probe can be extended on the basis of capturing the complementary sequence of the target region to obtain a Captured-Extension Product (CEP).

In the gene target region enrichment method, in the reaction of amplifying the fragmented DNA including the target region by a specific probe, the fragmented DNA including the target region may be one or more. Generally, there is a one-to-one correspondence between the specific probes and the fragmented DNA including the target region, that is, the number of specific probes in the reaction system may be one kind or multiple kinds. The extension described in this step refers to the entire pre-amplification step of the sample, including single or multiple rounds(cycles) of denaturation, annealing, and extension steps. In a preferred embodiment, in this step multiple cycles, such as 2-100, 2-10, 10-20, 20-30, 30-40, 40-60, 60-80, 80-100 cycles, are implements, in order to effectively increase the number of molecules containing the target area.

In the gene target region enrichment method, the fragmented DNA may be double-stranded DNA, single-stranded DNA, cDNA, etc. The cDNA may generally be obtained by reverse transcription of RNA. For double-stranded DNA, the specific probe may include a sequence complementary to the target region of one strand of the fragmented DNA. Therefore, the enrichment method of the present invention is also applicable to fragmented RNA. A person skilled in the art can perform subsequent operations through the enrichment method provided by the present invention after reverse-transcribing RNA into cDNA. The length of the fragmented DNA may be 25 to 200 bps, 25 to 40 bps, 40 to 60 bps, 60 to 80 bps, 80 to 100 bps, 100 to 120 bps, 120 to 140 bps, 140 to 160 bps, 160 to 180 bps, or 180 to 200 bps.

In the gene target region enrichment method, the amplification system of step (1) may include specific probes, DNA polymerase and dNTP. The reaction of amplifying the fragmented DNA including target region via a specific probe can usually be carried out in the presence of DNA polymerase. After the probe with 3' end blocking-modified binds to the template under the action of high-fidelity polymerase, the blocking group is excised, and the probe is reactivated so that the target sequence can be extended effectively. The DNA polymerase may have 3'-5' exonuclease activity, so that the substituent group at the 3' end of the probe after binding to the template can be cleaved, so that the probe can extend along the template. The DNA polymerase is preferably a high-fidelity DNA polymerase so as to further improve the amplification efficiency and purity of the product. The DNA polymerase may also be a common DNA polymerase (i.e., it does not have 3'-5' exonuclease activity). The amplification system in the step (1) further includes an active substance. The active substance can be used to excise the 3' terminal modification group of the specific probe after binding to the target region. The active substance can also be combined with DNA polymerase (for example, common DNA polymerase) in the captured-extension system to improve the efficiency of the amplification system. The active substance is preferably a nuclease. The reaction of amplifying the fragmented DNA including the target region by a specific probe can generally be carried out in the presence of dNTP, which can usually be a dNTP coupled with a labeling molecule. The labeling molecule can include but not limited to biotin and the like. The dTNP may include but not limited to dCTP, dATP and the like. The dNTP may also be coupled with a labeling molecule, which may be biotin or the like, and the labeling molecule may generally be used for purifying the captured-extension products.

In the gene target region enrichment method, the specific probe includes a sequence complementary to the target region of the fragmented DNA, thereby achieving specific amplification of the target region of the fragmented DNA. A person skilled in the art can select suitable target region for fragmented DNA, and design an appropriate complementary sequence according to the target region for fragmented DNA. The specific probe may be a specific probe whose 3' terminal nucleotide is modified, to prevent the 3' terminal of the specific probe from connecting with other groups, so as to avoid the free probe self-ligating or connecting other non-target molecules. For example, the non-target molecules may be linker DNA and the like. A person skilled in the art can select a suitable substituent group to modify the 3' terminal of the specific probe. For example, the modification group can replace the natural group (for example, hydroxyl group, etc.) on the 3' terminal nucleotide of the specific probe in order to prevent the ligation reaction at the 3' terminal of the specific probe. the modification group can usually be a blocking group. After the probe is combined with the target region on the template via the complementary sequence, the 3' end modification group can be cleaved by the enzyme, so that the probe is activated, and the target sequence can be effectively extended. The 3' terminal modification group of the specific probe may include, but not limited to, a hydrogen atom, a C3 Spacer group, a C6 Spacer group, a phosphate group ($PO_4$), an amino group ($NH_2$), etc. The choice of different substituent groups has obvious differences in the capture effect of the probe. In a preferred embodiment of the present invention, substituting the 3' terminal hydroxyl group of the probe with C3 Spacer gives the best effect, which has obvious advantages compared with other substituent groups. The specific probe also includes a universal sequence, which can usually be recognized by the sequencing system, so that the ligation products provided subsequently can be sequenced by the sequencing system. For example, for the Ion Torrent sequencing system, the universal sequence can be corresponding P1 sequence. In a preferred embodiment of the present invention, the base of the tail region of the 3' end of the specific probe may contain a mismatch, and the mismatched base may be the last base at the 3' end of the probe, or may be near the 3' end base. Mismatched base(s) can be a single base, or multiple bases. This mismatch instead of affecting the specificity and binding efficiency of the probe, will help to improve the cutting efficiency and fidelity of the high-fidelity DNA polymerase.

In the gene target region enrichment method, the step (1) may further include purification to the captured-extension product. A person skilled in the art may select a suitable method for purifying the captured-extension product. For example, the purification method for captured-extension product may include magnetic bead purification and the like.

In a specific embodiment of the present invention, the captured-extension product can be purified by a labeling molecule. A solid phase purification method of magnetic beads coated with avidin or streptavidin can be used in the purification process.

The gene target region enrichment method provided by the present invention may further include: connecting the 3' end of the captured-extension product provided in step (1) to a linker DNA to provide a ligation product.

In the gene target region enrichment method, a ligation system that connects the 3' end of the captured-extension product to the linker DNA may include a single-stranded ligase that causes the 5' end of the linker DNA connected to the 3' end of the captured-extension product. The single-stranded ligase is preferably T4 RNA ligase or thermostable RNA ligase or the like.

In the gene target region enrichment method, the linker DNA may be modified at the 5' terminal nucleotide and has a single-stranded structure at the reaction temperature of step (2), so that under the catalysis of the chain ligase, a covalent bond is formed between 3' end hydroxyl group of the captured-extension product and the 5' end modification group of the linker DNA and the ligation product is obtained. In a specific embodiment of the present invention, the 5' terminal nucleotide of the linker DNA (for example, the 5-position hydroxyl group of the 5' terminal nucleotide) is substituted with a phosphate group, thereby forming a phosphorylation modification. Under the catalysis of the single-stranded ligase, the 3' hydroxyl group of the captured-extension product and the phosphorylated 5' end of the linker DNA form a covalent bond to obtain the ligation product. In another specific embodiment of the present invention, the 5' terminal nucleotide of the linker DNA (for example, specifically the 5-position hydroxyl group of the 5' terminal nucleotide) is substituted with an adenosine group, thereby forming an adenylation modification. Under the catalysis of 5' App DNA/RNA thermostable ligase, the 5' end of the linker DNA can be ligated with the 3' end of the captured-extension product. In another specific embodiment of the present invention, the 5' terminal nucleotide of the linker DNA (for example, specifically the 5-position hydroxyl group of the 5' terminal nucleotide) is replaced with a phosphate group, thereby forming a phosphorylation modification. Under the catalysis of thermostable RNA ligase, the 5' terminal of the linker DNA can be ligated with the 3' end of the captured-extension product. The linker DNA may also be a partially double-stranded structure with a sticky end at the 5' end region, and the sticky end at the 5' end region has a single-stranded property, so that the 5' end can be modified by the method described above. Under the catalysis of a suitable single-stranded ligase, the 5' end can be linked to the captured-extension product. The linker DNA may also include one or more of a universal sequence, a sample tag sequence, a molecular tag sequence, etc. These sequences can usually be recognized by a sequencing system, so that the obtained ligation product can be sequenced. For example, for the Ion Torrent sequencing system, the universal sequence may be sequence A, the sample tag sequence may be barcode, and the molecular tag sequence corresponding thereto. Introducing barcode is helpful to distinguish samples from different sources in subsequent bioinformatics analysis, so that multiple samples can be sequenced simultaneously in a single reaction to increase throughput. The introduction of molecular tags facilitates the identification of different molecules in the subsequent bioinformatics analysis, so as to further identify the mutations generated in the subsequent amplification. The application of these sequences that can be recognized by the sequencing system enables the library of the present invention to be sequenced through the high-throughput sequencing platform to provide the information required for various subsequent research and clinical applications.

In a preferred embodiment of the present invention, the 3' end hydroxyl group of the linker DNA is also replaced by other groups to prevent the ligation reaction of the 3' end of the linker DNA to avoid self-ligation or connecting with non-target molecule, such as the free probe from step (1).

In the gene target region enrichment method, the step (2) may further include purification to the ligation product. A person skilled in the art may select a suitable method to purify the ligation product. For example, the purification method to the ligation product may include but not limited to silica gel column purification, heat treatment, and the like.

The gene target region enrichment method provided by the present invention can be used for gene detection. Methods for further genetic detection to the amplified ligation products are known to a person skilled in the art. In a specific embodiment of the present invention, the target region enrichment method can be applied to high-throughput sequencing. In another specific embodiment of the present invention, the method of enriching the target region of the present invention can be applied to the detection of gene sequences. For example, the target region includes: a site where the sequence is changed, and more specifically, a single base mutation site area, base deletion site area, base insertion site area and fusion mutation site area, etc. In another specific embodiment of the present invention, the method of enriching the target region of the present invention can be applied to the detection of the state of genetic modification. For example, the target region includes a region where methylation sites may exist, or, the DNA fragment has been treated with bisulfite.

The gene target region enrichment method provided by the present invention may further include: (3) amplifying the ligation product provided in the step (2). Generally, the ligation product can be PCR amplified via DNA polymerase and PCR amplification primers. By amplifying the ligation product, the product containing the DNA of the target region can be further enriched. A person skilled in the art may select a suitable method and system to amplify the ligation product provided in step (2), for example, the PCR amplification primer has a sequence matching the universal sequence of the specific probe and/or the universal sequence of the linker DNA. Specifically, the PCR amplification primer has a sequence that is at least partially complementary to the universal sequence of the specific probe and the universal sequence of the linker DNA.

The gene target region enrichment method provided by the present invention may further include: (4) sequencing the amplified ligation products to provide sequencing results of the target region. After PCR amplification of the ligation product, the amplification product can be sequenced by identifying the universal sequence in the amplification product to obtain the sequencing result of the target region. A person skilled in the art may select a suitable method and system to sequence the amplified ligation product, for example, sequencing the P1 sequence and the A sequence based on the Ion Torrent platform to obtain the sequencing result of the target region. It should be noted that the enrichment method of the present invention can make the ligation product obtained in step (2) contain any universal sequence for sequencing, such as Ion Torrent sequencing platform, Illumina sequencing platform, or other sequencing platforms.

The gene target region enrichment method provided by the present invention may further include: (5) detecting the ligation product provided in step (2) by the detection primer 1, the detection primer 2 and the probe 3, enabling the rapid detection of the target region by means of PCR instead of next-generation sequencing. At least one of the detection primer 1, the detection primer 2 and the probe 3 contains a gene-specific sequence, that is, for different gene target regions, the combination of the three primer/probe's specific sequences can be monospecific, bispecific or trispecific. In an embodiment of the present invention, the detection primer 1 includes a gene specific sequence, the detection primer 2 and the probe 3 include universal sequence; or the detection primer 1 and the detection primer 2 include a gene specific sequence; or the detection primer 1 and the probe 3 contains a gene specific sequence; or all of detection primer 1, detection primer 2, and probe 3 contain a gene specific sequence. In some embodiments, the probe 3 may further include a labeling molecule, such as a fluorescent molecule, and the sequence of the probe 3 is not complementary to the detection primer 1 or 2.

The second aspect of the present invention provides a kit for enriching target regions of fragmented DNA, including specific probes and linker DNA suitable for the gene target region enrichment method provided in the first aspect of the present invention. The structure of the specific probe and the linker DNA has been described in detail in the first aspect of the present invention, and will not be repeated here.

The kit provided by the present invention may further include one or more of the following components: RNA ligase, dNTP coupled with a labeling molecule, DNA polymerase, nuclease, etc. Among them, the RNA ligase can be a thermostable RNA ligase, T4 RNA ligase, or 5' App DNA/RNA thermostable ligase, and the like. dTNP can be dCTP or dATP. The DNA polymerase may be a DNA polymerase having 3'-5' exonuclease activity, preferably, the DNA polymerase is a high-fidelity polymerase.

The kit provided by the present invention may also include forward primers and reverse primers used for PCR amplification, which are generally matching the universal sequence of the specific probe and the universal sequence of the linker DNA. In particular, it may have a sequence at least partially complementary to the universal sequence of the specific probe and the universal sequence of the linker DNA.

The kit provided by the present invention may further include a detection primer 1, a detection primer 2 and a probe 3 for PCR detection, at least one of them contains a gene-specific sequence, such as monospecific, bispecific or trispecific primer/probe combinations. Preferably, only detection primer 1 contains a gene-specific sequence, refer to FIG. 4 for the detection process.

In a preferred embodiment of the present invention, after library construction by the method or kit of the present invention, as shown in FIG. 2, library molecules (for example, the ligation product provided in step (2), the structure may be as shown in FIG. 2) includes the following sequences in order: 5' end sequencing universal sequence, gene specific probe sequence, enriched target region sequence, adapter(linker) sequence, barcode, molecular tag sequence, 3' end sequencing universal sequence. The enriched target region contains the sequence information of the sample DNA before enrichment. The characteristics of this part of the sequence are as follows: the position of the 5' end on the genome is fixed and determined by the specific probe; while the position of the 3' end is not fixed, determined by the initial DNA fragmentation status of the library. Therefore, in the data analysis after enrichment, the position of the 3' end of the sequence on the genome can also serve as a molecular tag. Molecular tags can be used to distinguish different molecules and improve detection sensitivity and accuracy.

The beneficial effects of the present invention are as follows:

Firstly, before the ligation, the target regions of all fragmented DNA samples are pre-amplified by means of captured-extension, to avoid loss or missed detection of original target molecules (especially small fragments and rare molecules) caused by insufficient ligation efficiency of ligase during the ligation stage. The extension reaction in the pre-amplification stage is linear amplification and has no preference of PCR amplification, so, it will not accumulate errors introduced by PCR amplification. Compared with the conventional PCR library building technology, the product is more uniform and the subsequent sequencing results are more accurate.

Secondly, in the pre-amplification stage, only a single-stranded probe with a length of about 30 bp is necessary to be designed for each target gene, avoiding the difficulty of designing double-ended primers for short fragments such as cfDNA and shorter fragments such as ctDNA. Thus, not only the success rate of library construction but also the convenience of library construction is improved. Blocking the 3' end of the probe can block the non-intended ligation except the probe and the template, effectively reducing the background noise caused by the free probe, supplemented by the dNTP coupled to the labeling molecule and its purification system, the purity of the target product can be further improved and the sample DNA molecules can reach the theoretical maximum conversion rate.

Thirdly, after the 5' end of the linker DNA is modified, the linker DNA can be well connected to the 3' end of the extension product under the catalysis of single-stranded ligase but will not be connected to the 3' end of the block-modified specific probe. The 3' end of the linker is blocked to avoid the self-ligation or mis-ligation of the linker and increase the proportion of the target ligation product in the final product.

Finally, in the process of enriching the target region, the universal sequence for sequencing, the sample tag sequence and the molecular tag sequence are designed to be contained in the sequences of the probe and the linker, enabling direct sequencing and data analysis after library construction; or rapid PCR detection of the target region can be achieved using single, dual or trispecific primer/probe system.

In summary, the enrichment method and kit of the present invention are simple in operation and produces reliable results. The use of DNA with a fragment length of less than 200 bp can minimize the loss of original molecules, especially rare molecules, and enrich the target most efficiently. In addition, the enrichment method and kit have extremely High-fidelity, and the base error generated during the sequencing process can be effectively corrected through subsequent bioinformatics analysis, and the highest sequencing accuracy rate in theory can be achieved.

The following describes the embodiments of the present invention through specific examples. A person skilled in the art can easily understand other advantages and effects of the present invention from the contents disclosed in this specification. The present invention can also be implemented or applied through different specific embodiments. Based on different viewpoints and applications, the details in this specification can also be modified or changed without departing from the spirit of the present invention.

Before further describing the specific embodiments of the present invention, it should be understood that the scope of protection of the present invention is not limited to the specific embodiments described below. It should also be understood that the terms used in the examples of the present invention are intended to describe specific embodiments of the present invention, and are not intended to limit the scope of protection of the present invention. In the description and claims of the present invention, unless the context clearly indicates otherwise, the singular forms "a", "an", "one" and "this" include plural forms.

When the numerical ranges are given in the embodiments, it should be understood that unless the invention indicates otherwise, the two endpoints of each numerical range and any one value between the two endpoints can be selected. Unless otherwise defined, all technical and scientific terms used in the present invention have the same meaning as commonly understood by a person skilled in the art. In addition to the specific methods, equipment, and materials used in the embodiments, the methods, equipment, and materials described in the embodiments of the present invention can also be used according to the master of the prior art and the description of the present invention by a person skilled in the art. Similar or equivalent methods, devices and materials in prior art can also be used to implement the present invention.

Unless otherwise stated, the experimental methods, detection methods, and preparation methods disclosed in the present invention use conventional technologies in molecular biology, biochemistry, chromatin structure and analysis, analytical chemistry, cell culture, and reorganization DNA technology and related fields. These technologies have been well described in the existing literature. For details, see Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, etc.

Example 1

The oligonucleotide sequences used in Example 1 are shown in table 1:

TABLE 1

| Name | SEQ ID NO. | Sequence (5'→3') |
|---|---|---|
| Probe 1 | 1 | CCGCTTTCCTCTCTATGGGCAGTCGGTGAT CCTGGCAGCCAGGAACGTACTGGTGAA-OH |
| Probe 2 | 2 | CCGCTTTCCTCTCTATGGGCAGTCGGTGAT CCTGGCAGCCAGGAACGTACTGGTGAA-C3 Spacer |
| Probe 2p | 3 | CCGCTTTCCTCTCTATGGGCAGTCGGTGAT CCTGGCAGCCAGGAACGTACTGGTGAA-PO4 |

TABLE 1-continued

| Name | SEQ ID NO. | Sequence (5'→3') |
|---|---|---|
| Probe 2c | 4 | CCGCTTTCCTCTCTATGGGCAGTCGGTGAT CCTGGCAGCCAGGAACGTACTGGTGAA-C6 Spacer |
| Probe 2n | 5 | CCGCTTTCCTCTCTATGGGCAGTCGGTGAT CCTGGCAGCCAGGAACGTACTGGTGAA-NH$_2$ |
| Probe 2d | 6 | CCGCTTTCCTCTCTATGGGCAGTCGGTGAT CCTGGCAGCCAGGAACGTACTGGTGAA-DDC |
| Probe 3 | 7 | CCGCTTTCCTCTCTATGGGCAGTCGGTGAT CCTGGCAGCCAGGAACGTACTGGTGAT-C3 Spacer |
| Probe 4 | 8 | CCGCTTTCCTCTCTATGGGCAGTCGGTGAT CCTGGCAGCCAGGAACGTACTGrGTGAT-C3 Spacer |
| ABar-X1 | 9 | PO$_4$-GGATCCNNNNNNCAGCTTGGACTGAG TCGGAGACACGCAGGGATGAGATGG |
| ABar-X2 | 10 | PO$_4$-GGATCCNNNNNNGTTCTCCTTACTGA GTCGGAGACACGCAGGGATGAGATGG-C3 Spacer |
| ABar-X3 | 11 | 5'App-GGATCCNNNNNNTTACCTTAGCTG AGTCGGAGACACGCAGGGA TGAGATGG-C3 Spacer |
| EF-1 | 12 | GATCACAGATTTTGGGC |
| ER-1 | 13 | TTTGCCTCCTTCTGC |
| EM-1 | 14 | AACTGCTGGGTGCGGA |
| AF | 15 | GTCTCAGCCTCTCTATGGGCAGTCGGTGAT |
| AR | 16 | CCATCTCATCCCTGCGTGTCTCCGACTCAG |

The probe in this embodiment contains a universal sequence for sequencing (the bases marked in italics) and here contains the P1 sequence in the Ion Torrent sequencing system. The specific sequences of all probes in the table are directed to the L858R mutation of exon 21 of the EGFR gene. Among them, the probe 1 (SEQ ID NO.1) has no modification at the 3' terminal, and 3' terminal hydroxyl groups of probe 2, 3 and 4 (SEQ ID NO. 2, SEQ ID NO. 7, SEQ ID NO. 8) are replaced with C3 Spacer, 3' terminal hydroxyl group of probe 2p (SEQ ID NO. 3) is replaced with a phosphate group, 3' terminal hydroxyl group of probe 2c (SEQ ID NO. 4) is replaced with C6 Spacer, 3' terminal hydroxyl group of probe 2n (SEQ ID NO. 5) was replaced with a phosphate group, and 3' terminal hydroxyl group of probe 2d (SEQ ID NO. 6) is replaced with dideoxycytosine (DDC). Among them, the last base of probe 3 (SEQ ID NO. 7) is a mismatched base, and the G near the 3' end in probe 4 (SEQ ID NO. 8) is replaced with the RNA base rG.

The linker ABar-X1/2/3 (SEQ ID NO. 9, SEQ ID NO. 10, SEQ ID NO. 11) contains universal sequence for sequencing, which is the base marked in italics, here is Ion Torrent sequence A in the sequencing system. The underlined part of the sequence is barcode, which can be substituted with different barcodes in different samples of the present invention, and the changes in this part will not be repeated in the present invention. The "N" part is a molecular tag sequence, wherein NNNNNN is a random sequence used to label different extension product molecules in the same sample. The 5' terminal of the ABar-X1 and ABar-X2 (SEQ ID NO.

9, SEQ ID NO. 10) is phosphorylated modification. The 5' end of the ABar-X3 (SEQ ID NO. 11) is adenylation modification. The hydroxyl group at the 3' end of ABar-X2 and ABar-X3 (SEQ ID NO.10, SEQ ID NO.11) is substituted with C3 Spacer.

EF-1 and ER-1 (SEQ ID NO. 12, SEQ ID NO. 13) are the front and rear primers used for PCR detection of EGFR target sequence, wherein EM-1 (SEQ ID NO. 14) is MGB probe. AF and AR (SEQ ID NO. 15, SEQ ID NO. 16) are the front and rear primers used to amplify the library, respectively, and to match the universal sequence in the library, namely the P1 sequence in the probe and the A sequence in the linker.

Main Reagents and Materials

Figures 3, 4:
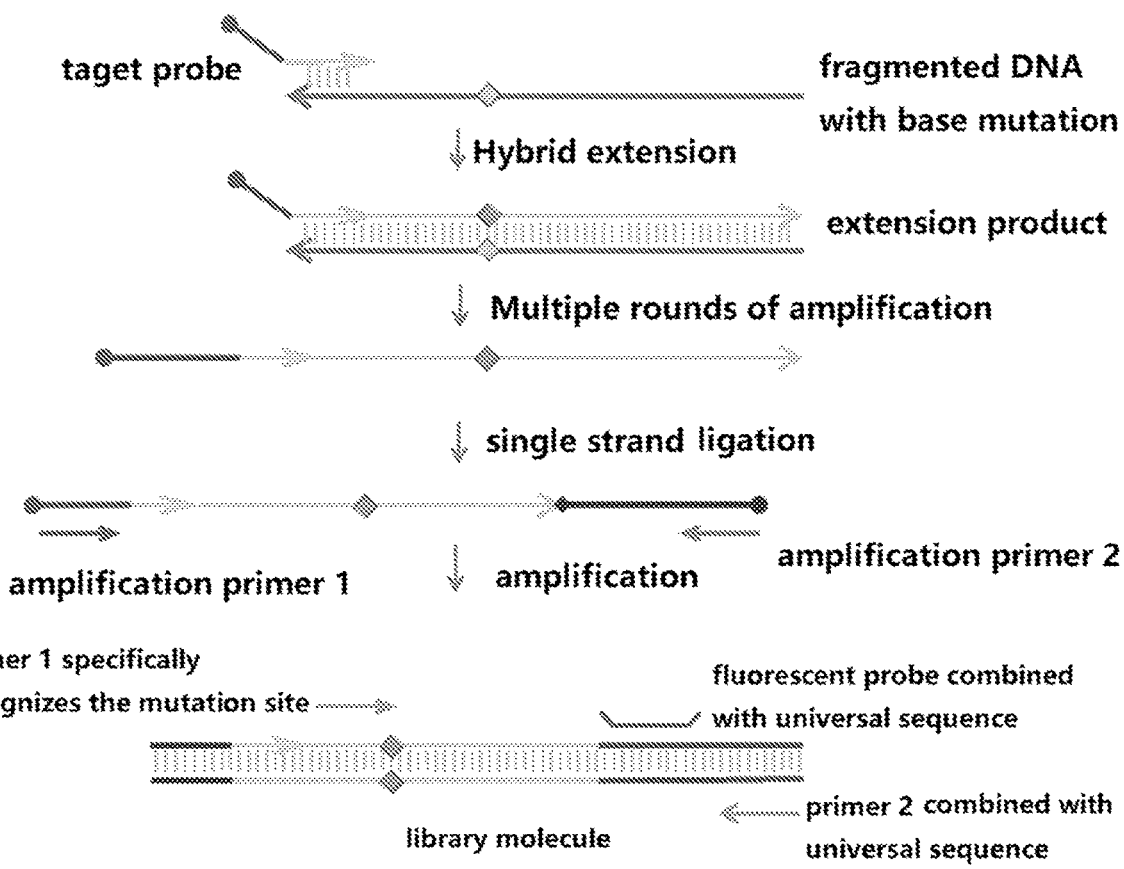
FIG. 3 is a schematic diagram of the construction of the calibrator in the embodiment of the present invention.
FIG. 4 is a schematic flowchart of a monospecific detection system in an embodiment of the present invention.

Plasma free DNA extraction kit was purchased from Qiagen; Cell DNA extraction kit and purified single-stranded DNA kit were RNA Clean Kit purchased from Tiangen Biotech; Thermally stable RNA ligase was purchased from Epicentre, USA; High-fidelity DNA polymerase reaction system, Biotin-dCTP and MyOne Strptavidin C1 reagent for purification were purchased from Invitrogen. DNA polymerase, high-fidelity DNA polymerase and PCR reaction kit were purchased from TOYOBO. RNAse $H_2$ thermostable nuclease was purchased from IDT. Q5 high-fidelity DNA polymerase, T4 RNA ligase and 5' App DNA/RNA thermostable ligase were purchased from NEB. Agencourt AMPure magnetic beads were purchased from Beckman. The calibrators for quantitative detection in the relevant process were constructed according to the conventional methods of molecular cloning, and the detailed composition is shown in FIG. 3.

Step 1. Sample Preparation

Extract cfDNA in healthy human plasma samples and DNA in NCI-H1975 cell line (this cell line is mutation of exon 21 of EGFR gene L858R) with extraction kit, and the DNA samples are quantified by Qubit Fluorometer quantifier. The DNA of the NCI-H1975 cell line was broken into fragments of about 160 bp, and mixed into the cfDNA samples of healthy people at the proportions of 10%, 1%, 0.1%, and 0.01%, and the cfDNA of healthy people was used as a blank control (QC).

Step 2. Captured-Extension

Prepare the captured-extension reaction system according to table 2, table 3, and table 4, respectively.

TABLE 2

| Compositions | Volume (μL) | Final Concentration |
| --- | --- | --- |
| 2× high-fidelity DNA polymerase PCR Master Mix (with 3'-5' exonuclease activity); or, 2× DNA polymerase PCR Master Mix (without 3'-5' exonuclease activity) | 25 | 1× |
| Specific probe (10 μM) | 0.5 | 100 nM |
| cfDNA samples of all types | 20 | 20000 copies |
| $H_2O$ | 4.5 | / |
| Total | 50 | / |

TABLE 3

| Compositions | Volume (μL) | Final Concentration |
| --- | --- | --- |
| 2× DNA polymerase PCR Master Mix (without 3'-5' exonuclease activity) | 25 | 1× |
| RNAse $H_2$ thermostable nuclease | 0.5 | / |
| Specific probe (10 μM) | 0.5 | 100 nM |
| cfDNA samples of all types | 20 | 20000 copies |
| $H_2O$ | 4 | / |
| Total | 50 | / |

TABLE 4

| Compositions | Volume (μL) | Final Concentration |
| --- | --- | --- |
| 2× high-fidelity DNA polymerase PCR Master Mix (with 3'-5' exonuclease activity) | 25 | 1× |
| Specific probe (10 μM) | 0.5 | 100 nM |
| Biotin-dCTP (0.4 mM) | 2.5 | 20 μM |
| cfDNA samples of all types | 20 | 20000 copies |
| $H_2O$ | 2 | / |
| Total | 50 | / |

The PCR procedure of captured-extension is shown in Table 5:

TABLE 5

| Cycles | Temperature | Time |
| --- | --- | --- |
| 1 cycle | 98° C. | 60 s |
| 1/20/40 cycles | 98° C. | 10 s |
| | 67° C. | 20 s |
| | 72° C. | 20 s |
| 1 cycle | 72° C. | 5 min |

After completion of the captured-extension process, the extension product was purified by silica gel column using RNA Clean kit and eluted with 60 μL of the elution buffer. (The silica gel column purification mentioned hereafter in the present invention is the same). The extension product was further purified with the magnetic beads coated with streptavidin after the silica gel column purification, and finally all the products are dissolved in 60 μL elution buffer.

Step 3. Extension Efficiency Detection

Prepare PCR detection system for extension products according to table 6.

TABLE 6

| Compositions | Volume (μL) | Final Concentration |
| --- | --- | --- |
| 2× Taqman Mix | 25 | 1× |
| ER-1 (10 μM) | 1.5 | 300 nM |
| AF (10 μM) | 1.5 | 300 nM |
| EM-1 (10 μM) | 0.5 | 100 nM |
| $H_2O$ | 17.5 | / |
| Extension product/Calibrator | 4 | / |
| Total Volume | 50 | / |

The PCR procedure for detecting the extension efficiency is shown in table 7.

TABLE 7

| Cycles | Temperature | Time |
| --- | --- | --- |
| 1 cycle | 95° C. | 3 min |
| 45 cycles | 95° C. | 10 s |
|  | 56° C. | 25 s |
|  | 72° C. | 20 s |

Step 4. Single-Stranded Ligation

According to the results of step 3, select part of the extension product obtained in step 2 to prepare the ligation reaction system according to table 8, table 9, and table 10, respectively.

TABLE 8

| Compositions | Volume (μL) | Final Concentration | Ligation Conditions |
| --- | --- | --- | --- |
| CircLigase II 10× Reaction Buffer | 4 | 1× | 60° C. 1 hour |
| 50 mM MnCl$_2$ | 2 | 2.5 mM |  |
| 5M Betaine | 8 | 1 M |  |
| Thermostable RNA ligase (100 U/μL) | 2 | 5 U/μL |  |
| ABar-X1/ABar-X2 (200 nM) | 2 | 10 nM |  |
| Extension product | 8 |  |  |
| 50% PEG | 14 | 17.5% |  |
| Total | 40 | / |  |

TABLE 9

| Compositions | Volume (μL) | Final Concentration | Ligation Conditions |
| --- | --- | --- | --- |
| 10× Buffer for ligation | 4 | 1× | 16° C. 4 hours |
| T4 RNA ligase | 2 | 5 U/μL |  |
| Linker ABar-X2 (200 nM) | 2 | 10 nM |  |
| Extension Product | 8 | / |  |
| 50% PEG | 14 | 17.5% |  |
| Total | 40 | / |  |

TABLE 10

| Compositions | Volume (μL) | Final Concentration | Ligation Conditions |
| --- | --- | --- | --- |
| 10× NE Buffer 1 | 4 | 1× | 65° C. 1 hour |
| 50 mM MnCl$_2$ | 2 | 2.5 mM |  |
| H$_2$O | 8 | / |  |
| 5'App DNA/RNA thermostable ligase (100 U/μL) | 2 | 5 U/μL |  |
| Linker ABar-X3 (200 nM) | 2 | 10 nM |  |
| Captured-Extension Product | 8 |  |  |
| 50% PEG | 14 | 17.5% |  |
| Total | 40 | / |  |

Processing after obtaining the ligation product is shown in table 11.

TABLE 11

| Process 1 | Process 2 | Process 3 |
| --- | --- | --- |
| None (as control) | Incubating for 10 min at 95° C. | Purification using silica gel column |

Step 5. Test of the Ligation Efficiency

Prepare the PCR system for testing the ligation efficiency of step 4 according to table 12.

TABLE 12

| Reagent | Dosage (μL) | Final Concentration |
| --- | --- | --- |
| 2× Taqman Mix | 12.5 | 1× |
| AF (10 μM) | 0.75 | 300 nM |
| AR (10 μM) | 0.75 | 300 nM |
| EM-1 (10 μM) | 0.25 | 100 nM |
| H$_2$O | 8.75 | / |
| Calibrator/Ligation Product | 2 | / |
| Total | 25 | / |

PCR reaction conditions for testing the ligation efficiency is shown in table 13.

TABLE 13

| Cycles | Temperature | Time |
| --- | --- | --- |
| 1 cycle | 95° C. | 4 min |
| 45 cycles | 95° C. | 10 s |
|  | 60° C. | 30 s |
|  | 72° C. | 20 s |

Step 6. Amplification of the Library

Amplify the ligation product obtained in step 4 with PCR according to the reaction conditions and procedure as shown in table 14.

TABLE 14

| Compositions | Volume (μL) |
| --- | --- |
| Ligation product | 30 |
| 5× Q5 Buffer | 10 |
| dNTP (10 mM each) | 1 |
| Q5 high-fidelity DNA polymerase (2 U/uL) | 1 |
| AF (10 μM) | 1.5 |
| AR (10 μM) | 1.5 |
| ddH$_2$O | 5 |
| Total Volume | 50 |

| Temperature (° C.) | Time(s) | Cycles |
| --- | --- | --- |
| 98 | 30 | 1 |
| 98 | 10 | 15 |
| 72 | 30 |  |
| 72 | 300 | 1 |

Purify the amplified library with 80 μL of Agencourt AMPure magnetic beads, and dissolve the purified amplified product in 30 μL of elution buffer. At this point, the library construction is completed, and the library is ready for sequencing.

Step 7. Sequencing and Data Analysis

Sequencing the prepared library on the Ion Proton sequencer. Related operations include water-in-oil PCR, library enrichment, chip loading, and on-board sequencing. For detailed operation procedures, see Ion PI™ Hi-Q™ OT2 200 Kit manual and Ion PI™ Hi-Q™ Sequencing 200 Kit manual.

Experimental Results and Analysis

The calculation method of captured-extension multiple (magnification), capture efficiency and ligation efficiency in the results is as follows:

Captured-extension magnification=EGFR gene output copies after capture/EGFR gene input copies before capture Capture efficiency=(Captured-extension multiple-1)/Captured-extension cycles×100%   (5)

Ligation efficiency=(output copies of ligation product/input copies of extension product)×100%

The analysis of all process data (such as capture efficiency, ligation efficiency) in this embodiment comes from QC samples.

Results 1. The Effect of Different Types of Polymerases on the Captured-Extension Results of Different Probes.

TABLE 15

Testing results of different types of polymerases for captured-extension (QC sample)

| Probe | Types of DNA polymerases | Nuclease | Cycles | Copies of EGFR output after captured-extension | Copies of EGFR input before captured-extension | Captured-extension Multiple | Capture Efficiency % |
|---|---|---|---|---|---|---|---|
| Probe 1 | High-fidelity polymerase | N | 40 | 482000 | 20000 | 24.1 | 57.75% |
| Probe 2 | High-fidelity polymerase | N | 40 | 566000 | 20000 | 28.3 | 68.25% |
| Probe 2p | High-fidelity polymerase | N | 40 | 98400 | 20000 | 4.92 | 9.80% |
| Probe 2c | High-fidelity polymerase | N | 40 | 428000 | 20000 | 21.4 | 51% |
| Probe 2n | High-fidelity polymerase | N | 40 | 64800 | 20000 | 3.24 | 5.6% |
| Probe 2d | High-fidelity polymerase | N | 40 | 71200 | 20000 | 3.56 | 6.4% |
| Probe 3 | High-fidelity polymerase | N | 40 | 524000 | 20000 | 26.2 | 63.00% |
| Probe 4 | High-fidelity polymerase | N | 40 | 482000 | 20000 | 24.1 | 57.75% |
| Probe 1 | Common polymerase | N | 40 | 512000 | 20000 | 25.6 | 61.50% |
| Probe 2 | Common polymerase | N | 40 | 24000 | 20000 | 1.2 | 0.50% |
| Probe 2p | Common polymerase | N | 40 | 21000 | 20000 | 1.05 | 0.12% |
| Probe 2c | High-fidelity polymerase | N | 40 | 21000 | 20000 | 1.1 | 0.25% |
| Probe 2n | High-fidelity polymerase | N | 40 | 23000 | 20000 | 1.15 | 0.38% |
| Probe 2d | High-fidelity polymerase | N | 40 | 24000 | 20000 | 1.20 | 0.5% |
| Probe 3 | Common polymerase | N | 40 | 22000 | 20000 | 1.1 | 0.25% |
| Probe 4 | Common polymerase | N | 40 | 26000 | 20000 | 1.3 | 0.75% |
| Probe 1 | Common polymerase | Y | 40 | 496000 | 20000 | 24.8 | 59.50% |
| Probe 2 | Common polymerase | Y | 40 | 26000 | 20000 | 1.3 | 0.75% |
| Probe 3 | Common polymerase | Y | 40 | 22000 | 20000 | 1.1 | 0.25% |
| Probe 4 | Common polymerase | Y | 40 | 506000 | 20000 | 25.3 | 60.75% |

The captured-extension reaction system involved in table 15 is shown in table 2 and table 3, wherein, the high-fidelity polymerase is 2× high-fidelity DNA polymerase PCR Master Mix (DNA polymerase has 3'-5' exonuclease activity), the common polymerase is 2×DNA polymerase PCR Master Mix (DNA polymerase does not have 3'-5' exonuclease activity), the cfDNA sample used is QC sample, please refer to step 3 for the method of extension efficiency detection.

It can be seen from the test results: 1) After the 3' end-blocking modified probe binds to the template under the action of high-fidelity polymerase, the blocking group is excised and the probe is activated, so that the target sequence can be extended effectively; 2) Combination of thermostable nuclease and common polymerase play an activation effect to the probe with modified RNA, enhancing the applicability of the enrichment method of the present invention; 3) Selection of different substitution groups has obvious differences in the capture effect of the probe. Substituting the 3' terminal hydroxyl group of the probe with C3 Spacer gives the best effect, which has obvious advantages compared with other substituent groups. Therefore, the data from result 2 in this example mainly refers to the result data obtained for the probe in which the 3' terminal hydroxyl group is replaced by C3 Spacer.

Result 2. The Effect of Different Extension Cycles on Probe Extension Results.

TABLE 16

Test results of different extended cycles (QC sample)

| Probe | Types of DNA polymerases | Nuclease | Cycles | Copies of EGFR output after captured-extension | Copies of EGFR input before captured-extension | Captured-extension Magnification | Capture Efficiency % |
|---|---|---|---|---|---|---|---|
| Probe 1 | High-fidelity polymerase | N | 40 | 482000 | 20000 | 24.1 | 57.75% |
| Probe 2 | High-fidelity polymerase | N | 40 | 566000 | 20000 | 28.3 | 68.25% |
| Probe 3 | High-fidelity polymerase | N | 40 | 524000 | 20000 | 26.2 | 63.00% |
| Probe 4 | High-fidelity polymerase | N | 40 | 482000 | 20000 | 24.1 | 57.75% |
| Probe 1 | High-fidelity polymerase | N | 20 | 276000 | 20000 | 13.8 | 64.00% |
| Probe 2 | High-fidelity polymerase | N | 20 | 244000 | 20000 | 12.2 | 56.00% |
| Probe 3 | High-fidelity polymerase | N | 20 | 234000 | 20000 | 11.7 | 53.50% |
| Probe 4 | High-fidelity polymerase | N | 20 | 248000 | 20000 | 12.4 | 57.00% |
| Probe 1 | High-fidelity polymerase | N | 1 | 34800 | 20000 | 1.74 | 74.00% |
| Probe 2 | High-fidelity polymerase | N | 1 | 34400 | 20000 | 1.72 | 72.00% |
| Probe 3 | High-fidelity polymerase | N | 1 | 36400 | 20000 | 1.82 | 82.00% |
| Probe 4 | High-fidelity polymerase | N | 1 | 31400 | 20000 | 1.57 | 57.00% |

The captured-extension system referred to in Table 16 is disclosed in Table 2. The cfDNA sample used in the result is the QC sample. The method for testing the extension efficiency is shown in step 3.

The results showed that the Captured-extension magnification can be effectively increased by increasing the extension cycles.

Result 3. Effect of dNTP Coupling with Labeling Molecule on the Captured-Extension Performance

TABLE 17

Test results of captured-extension system with Biotin-dCTP mixed (QC sample)

| Probe | Types of DNA polymerases | Purification system with Biotin-dCTP mixed | Cycles | Copies of EGFR output with biotin labelled | Copies of EGFR input before capture | Captured-extension Magnification | Capture Efficiency % |
|---|---|---|---|---|---|---|---|
| Probe 1 | High-fidelity polymerase | N | 40 | 0 | 20000 | 0 | / |
| Probe 2 | High-fidelity polymerase | N | 40 | 0 | 20000 | 0 | / |

TABLE 17-continued

Test results of captured-extension system with Biotin-dCTP mixed (QC sample)

| Probe | Types of DNA polymerases | Purification system with Biotin-dCTP mixed | Cycles | Copies of EGFR output with biotin labelled | Copies of EGFR input before capture | Captured-extension Magnification | Capture Efficiency % |
|---|---|---|---|---|---|---|---|
| Probe 3 | High-fidelity polymerase | N | 40 | 0 | 20000 | 0 | / |
| Probe 4 | High-fidelity polymerase | N | 40 | 0 | 20000 | 0 | / |
| Probe 1 | High-fidelity polymerase | Y | 40 | 212000 | 20000 | 10.6 | 24.00% |
| Probe 2 | High-fidelity polymerase | Y | 40 | 183000 | 20000 | 9.15 | 20.38% |
| Probe 3 | High-fidelity polymerase | Y | 40 | 198000 | 20000 | 9.9 | 22.25% |
| Probe 4 | High-fidelity polymerase | Y | 40 | 187000 | 20000 | 9.35 | 20.88% |

The captured-extension system referred to in Table 17 is disclosed in Table 2 and 4. The cfDNA sample used in the result is the QC sample. The method for testing the extension efficiency is shown in step 3.

The results showed that the extension products can be labelled effectively and the Capture Efficiency can be effectively increased by mixing dCTP coupling with biotin.

Result 4. Effect of dNTP Coupling with Labeling Molecule on the Ligation Efficiency

TABLE 18

Test result of the ligation reaction after mixing Biotin-dCTP into the captured-extension system (QC)

| Probe | Purification system with Biotin-dCTP mixed | linker | ligase | Purification method after ligation | Copies of extension input | Copies of ligation output | Ligation Efficiency |
|---|---|---|---|---|---|---|---|
| Probe 1 | N | ABar-X2 | Thermostable RNA ligase | Silica gel column | 77120 | 84 | 0.11% |
| Probe 2 | N | ABar-X2 | Thermostable RNA ligase | Silica gel column | 90560 | 1452 | 1.60% |
| Probe 3 | N | ABar-X2 | Thermostable RNA ligase | Silica gel column | 83840 | 1878 | 2.24% |
| Probe 1 | Y | ABar-X2 | Thermostable RNA ligase | Silica gel column | 28267 | 328 | 1.16% |
| Probe 2 | Y | ABar-X2 | Thermostable RNA ligase | Silica gel column | 24400 | 13257 | 54.33% |
| Probe 3 | Y | ABar-X2 | Thermostable RNA ligase | Silica gel column | 26400 | 17328 | 65.64% |

The ligation system referred to in Table 18 is shown in Table 8, wherein the extension product is prepared according to the system of Table 2 or 4, wherein high-fidelity polymerase is used in each system and the high-fidelity polymerase is 2× high-fidelity DNA polymerase PCR Master Mix (with a 3'-5' exonuclease activity). The cfDNA sample used is QC sample. The method for testing the ligation efficiency is shown in step 5.

The results showed that probes with 3' terminal hydroxyl group substituted by C3 Spacer in combination with using the dCTP coupled with biotin and a purification system targeting the biotin gives the best results; while in systems comprising probes without substituent group or dNTP without biotin, almost unable to ligate(connect).

Result 5. Effect of Probes with Different 5' Terminal Substitution and the Use of Different Ligases on the Ligation Efficiency.

TABLE 19

Test results of probes with different 5' terminal substitution and different ligases in the ligation system (QC sample)

| Probe | Purification system with Biotin-dCTP mixed | Linker | Ligase | Purification method after ligation | Copies of extension input | Copies of ligation output | Ligation Efficiency |
|---|---|---|---|---|---|---|---|
| Probe 2 | Y | ABar-X2 | Thermostable RNA ligase | Silica gel column | 24400 | 13257 | 54.33% |
| Probe 3 | Y | ABar-X2 | Thermostable RNA ligase | Silica gel column | 26400 | 17328 | 65.64% |
| Probe 2 | Y | ABar-X2 | T4 RNA | Silica gel column | 24400 | 2264 | 9.28% |
| Probe 3 | Y | ABar-X2 | T4 RNA | Silica gel column | 26400 | 2828 | 10.71% |
| Probe 2 | Y | ABar-X3 | 5'AppDNA/RNA ligase | Silica gel column | 24400 | 2073 | 8.50% |
| Probe 3 | Y | ABar-X3 | 5'AppDNA/RNA ligase | Silica gel column | 26400 | 2154 | 8.16% |

The ligation system referred to in Table 19 is shown in Table 8, 9 and 10, wherein the extension product is prepared according to the system of Table 4. The cfDNA sample used is the QC sample. The method for testing the ligation efficiency is shown in step 5.

The results showed that probes with phosphorylated 5' terminal in combination with a thermostable RNA ligase can significantly improve the ligation efficiency.

Result 6. Effect of Linker DNAs with Different 3' Terminal Substitution on the Ligation Efficiency.

TABLE 20

Test results of linker DNAs with different 3' terminal substitution in the system (QC sample)

| Probe | Purification system with Biotin-dCTP mixed | Linker | Ligase | Purification method after ligation | Copies of extension input | Copies of ligation output | Ligation Efficiency |
|---|---|---|---|---|---|---|---|
| Probe 2 | Y | ABar-X2 | Thermostable RNA ligase | Silica gel column | 24400 | 13257 | 54.33% |
| Probe 3 | Y | ABar-X2 | Thermostable RNA ligase | Silica gel column | 26400 | 17328 | 65.64% |
| Probe 2 | Y | ABar-X1 | Thermostable RNA ligase | Silica gel column | 24400 | 4321 | 17.71% |
| Probe 3 | Y | ABar-X1 | Thermostable RNA ligase | Silica gel column | 26400 | 3875 | 14.68% |

The ligation system referred to in Table 20 is shown in Table 8, wherein the extension product is prepared according to Table 4. The cfDNA sample used is the QC sample. The method for testing the ligation efficiency is shown in step 5.

The results showed that linkers with blocked 3' terminal significantly improves the ligation efficiency by reducing self-ligation and mis-ligation.

Result 7. Effect of Different Purification Methods after Ligation on the Proportion of the Target Product.

TABLE 21

Results of the proportion of the target product by using different purification methods after ligation (QC sample)

| Probe | Purification system with Biotin-dCTP mixed | Linker | Ligase | Purification method after ligation | Copies of extension input | Copies of ligation output | proportion of the target product |
|---|---|---|---|---|---|---|---|
| Probe 2 | Y | ABar-X2 | Thermostable RNA ligase | Silica gel column | 24400 | 13257 | 54.33% |
| Probe 3 | Y | ABar-X2 | Thermostable RNA ligase | Silica gel column | 26400 | 17328 | 65.64% |
| Probe 2 | Y | ABar-X2 | Thermostable RNA ligase | Heating | 24400 | 10567 | 43.31% |
| Probe 3 | Y | ABar-X2 | Thermostable RNA ligase | Heating | 26400 | 12385 | 46.91% |
| Probe 2 | Y | ABar-X2 | Thermostable RNA ligase | None | 24400 | 2324 | 9.52% |
| Probe 3 | Y | ABar-X2 | Thermostable RNA ligase | None | 26400 | 2875 | 10.89% |

The ligation system referred to in Table 21 is shown in Table 8, wherein the extension product is prepared according to Table 4. The cfDNA sample used is the QC sample. The specific parameters of purification method used after ligation is shown in Table 11. The method for testing the ligation efficiency is shown in step 5.

The results showed that after the ligation reaction, either the silica gel column purification or heating purification can effectively remove or reduce the amount of residual thermostable RNA ligase in the ligation products, thereby reducing the background noise in ligation products and increasing the proportion of the target product.

Result 8. Data of the Samples Under Different Reaction Conditions.

The reaction conditions for the sequencing analysis are shown in Table 22. The sequencing method is disclosed in step 7. The results of the sequencing analysis corresponding to the conditions as stated in Table 22 are shown in Table 23. The detection results in the mutant DNA mixing with cfDNA with different ratios are shown in Table 24.

TABLE 22

Reaction conditions of the sequencing analysis

| Condition Number | Probe | Type of DNA polymerase | Nuclease | Cycles | Purification system with Biotin-dCTP mixed | Linker | Ligase | Process after ligation |
|---|---|---|---|---|---|---|---|---|
| 1 | Probe 1 | High-fidelity polymerase | N | 40 | Y | ABar-X2 | Thermostable RNA ligase | Silica gel column |
| 2 | Probe 2 | High-fidelity polymerase | N | 40 | Y | ABar-X2 | Thermostable RNA ligase | Silica gel column |
| 3 | Probe 2p | High-fidelity polymerase | N | 40 | Y | ABar-X2 | Thermostable RNA ligase | Silica gel column |
| 4 | Probe 3 | High-fidelity polymerase | N | 40 | Y | ABar-X2 | Thermostable RNA ligase | Silica gel column |
| 5 | Probe 4 | Common polymerase | Y | 40 | Y | ABar-X2 | Thermostable RNA ligase | Silica gel column |
| 6 | Probe 3 | High-fidelity polymerase | N | 40 | N | ABar-X2 | Thermostable RNA ligase | Silica gel column |
| 7 | Probe 3 | High-fidelity polymerase | N | 40 | Y | ABar-X1 | Thermostable RNA ligase | Silica gel column |

TABLE 22-continued

Reaction conditions of the sequencing analysis

| Condition Number | Probe | Type of DNA polymerase | Nuclease | Cycles | Purification system with Biotin-dCTP mixed | Linker | Ligase | Process after ligation |
|---|---|---|---|---|---|---|---|---|
| 8 | Probe 3 | High-fidelity polymerase | N | 40 | Y | ABar-X2 | T4 RNA | Silica gel column |
| 9 | Probe 3 | High-fidelity polymerase | N | 40 | Y | ABar-X3 | 5'AppDNA/ RNA ligase | Silica gel column |
| 10 | Probe 3 | High-fidelity polymerase | N | 40 | Y | ABar-X2 | Thermostable RNA ligase | Heating |
| 11 | Probe 3 | High-fidelity polymerase | N | 40 | Y | ABar-X2 | Thermostable RNA ligase | None |

The ligation products provided by the PCR amplification as described in Table 22 are the ligation products by further preparing the extension products provided according to the systems in Table 3 and 4 according to the ligation reaction system in Tables 8 to 10. The specific parameters of the purification method used after ligation is disclosed in Table 11. The cfDNA samples referred to in the sequencing results in Table 23 are the QC samples. In the test of mixing mutant DNA into cfDNA at different ratio in Table 24, for the same condition number, except that DNA of NCI-H1975 cell line are mixed into cfDNA in different amount, the experimental steps are the same as in Table 22.

TABLE 23

Results of sequencing analysis

| | Condition Number | | | | | | | | | | |
|---|---|---|---|---|---|---|---|---|---|---|---|
| | 1 | 2 | 3 | 4 | 5 | 6 | 7 | 8 | 9 | 10 | 11 |
| Total reads | 367842 | 245740 | 284632 | 345320 | 299538 | 327782 | 243698 | 288673 | 296643 | 308712 | 312156 |
| Reads aligning to hg19 | 184 | 211600 | 2343 | 327080 | 275605 | 1052 | 30292 | 126641 | 70809 | 270555 | 35336 |
| Alignment rate | 0.05% | 86.11% | 0.82% | 94.72% | 92.01% | 0.32% | 12.43% | 43.87% | 23.87% | 87.64% | 11.32% |
| Reads from the target region | 61 | 125072 | 1039 | 192654 | 144252 | 402 | 14004 | 67436 | 34965 | 149671 | 16247 |
| Ratio of reads from the target region | 33.40% | 59.11% | 44.37% | 58.90% | 52.34% | 38.20% | 46.23% | 53.25% | 49.38% | 55.32% | 45.98% |

TABLE 24

Results of detection of mutant DNA in cfDNA under different mix rates

| | Condition Number | | | | | | | | | | |
|---|---|---|---|---|---|---|---|---|---|---|---|
| | 1 | 2 | 3 | 4 | 5 | 6 | 7 | 8 | 9 | 10 | 11 |
| 0 mixed | 0 | 0 | 0 | 0 | 0 | 0 | 0 | 0 | 0 | 0 | 0 |
| 0.01% mixed | 0 | 0.012% | 0 | 0.021% | 0.009% | 0 | 0 | 0 | 0 | 0.019% | 0 |
| 0.1% mixed | 0 | 0.13% | 0 | 0.12% | 0.14% | 0 | 0.08% | 0.11% | 0.09% | 0.12% | 0.08% |
| 1% mixed | 0 | 1.15% | 0.48% | 1.08% | 0.83% | 0 | 1.12% | 1.13% | 1.11% | 1.18% | 1.13% |
| 10% mixed | 2.30% | 10.25% | 9.53% | 10.22% | 9.89% | 5.21% | 10.13% | 10.23% | 9.54% | 10.22% | 10.15% |

It can be seen from Table 23 and Table 24, under the reaction conditions numbered 2, 4, 5, and 10, the sequencing alignment rates and the sensitivities are high, and the mutation can be correctly detected in the cfDNA sample with a mixing ratio of as low as 0.01%. The results showed that the blocking modification of the 3' terminal hydroxyl group of the probes is essential to prevent self-ligation or ligating to the linker, which significantly reduces the background noise. After binding to the template, the substituent group of the probe can be cleaved and the bound probe can effectively extend. The dNTP coupled with labeling molecule and a purification system thereof can significantly improve the purity of the target product in the final library. In addition, the application of thermostable RNA ligase, the blocking of the 3' terminal of the linker, and the purification after ligation can further improve the purity of the final library product and the sensitivity of detection, respectively/together constitute the technical solution of the present invention.

Embodiment 2

The oligonucleotide sequences used in embodiment 2 are shown in table 25.

TABLE 25

| Name | SEQ ID NO: | Sequence (5'→3') |
|---|---|---|
| Probe 5 | 17 | CCGCTTTCCTCTCTATGGGCAGTCGGTGAT TAGTTGGATGGGATTATTT-C3 Spacer |
| Probe 6 | 18 | CCGCTTTCCTCTCTATGGGCAGTCGGTGAT TTTTTTTTGGGAGTTTAAATAAAGATTA-C3 Spacer |
| Probe 7 | 19 | CCGCTTTCCTCTCTATGGGCAGTCGGTGAT TTTAAAATAGAGTTAGTTTTAGTTTTT-C3 Spacer |
| ABar-X2 | 10 | PO4-GGATCCNNNNNNGTTCTCCTTACTGA GTCGGAGACACGCAGGGATGAGATGG-C3 Spacer |
| AF | 15 | GTCTCAGCCTCTCTATGGGCAGTCGGTGAT |
| AR | 16 | CCATCTCATCCCTGCGTGTCTCCGACTCAG |

The probes in this example comprise a universal sequence, that is, bases shown in italic, which is the P1 sequence of the Ion Torrent system. The DNA sample used in this embodiment has been treated with bisulfite. Probe 5 (SEQ ID NO 17) targets a methylation region of the gene SEPT9, Probe 6 (SEQ ID NO: 18) targets a methylation region of the gene NDRG4, and Probe 7 (SEQ ID NO: 19) targets a methylation region of the gene BMP3.

The linker ABar-X2 (SEQ ID NO. 10) comprises a universal sequence, that is, bases shown in italic, which is the A sequence of the Ion Torrent system. The sequence underlined is a barcode, which can be replaced with different barcodes in different samples in the present invention. The "N" sequence is a molecular tag sequence (UMI), in which NNNNNN is a random sequence that is used to label different extension product molecules in the same sample. The 5' terminal of the linkers ABar-X2 (SEQ ID NO. 10) is phosphorylated.

AF (SEQ ID NO.15) and AR (SEQ ID NO.16) are the PCR pre-primers and post-primers used to amplify the library, respectively. The sequences thereof were matching the universal sequences (that is, the P1 sequence and the A sequence) in the library molecule.

Reagents and Materials

The bisulfite conversion kit was purchased from Promega. The Agencourt AMPure magnetic beads were purchased from Beckman. The other main reagents used were the same as in embodiment 1.

Step 1. Preparation of the Sample

Five samples of healthy people's plasma samples and intestinal cancer tissue samples were extracted, and the DNA samples were quantified by Qubit Fluorometer. The DNA from intestinal cancer tissues was sheared into fragments of about 160 bp and mixed into the plasma sample of healthy individuals at ratios of 10% and 5% to provide samples of 5% mixing rate and 10% mixing rate. Plasma sample from healthy individuals was used as a blank. Convert the plasma samples of healthy individuals using the Promega bisulfite conversion system. The converted DNA was quantified and formulated into a concentration of 1000 copies/μL.

Step 2. Captured-Extension

Prepare the captured-extension system according to table 26.

TABLE 26

| Compositions | Volume (μL) | Final Concentration |
|---|---|---|
| 2X High-fidelity DNA polymerase PCR Master Mix (with 3'-5' exonuclease activity) | 25 | 1× |
| Probe 5 (10 μM) | 0.5 | 100 nM |
| Probe 6 (10 μM) | 0.5 | 100 nM |
| Probe 7 (10 μM) | 0.5 | 100 nM |
| cfDNA samples | 20 | 20000 copies |
| H$_2$O | 3.5 | / |
| Total | 50 | / |

PCR reaction conditions of the captured-extension system is shown in table 27.

TABLE 27

| Cycles | Temperature | Time |
|---|---|---|
| 1 cycle | 98° C. | 60 s |
| 40 cycles | 98° C. | 10 s |
|  | 62° C. | 20 s |
|  | 72° C. | 20 s |
| 1 cycle | 72° C. | 5 min |

After completion of the captured-extension, the extension product was purified by silica gel column and eluted with 60 μL of the elution buffer. The captured-extension product in table 4 was further purified with the magnetic beads coated with streptavidin after the silica gel column purification, and finally dissolved in elution buffer of 60 μL.

Step 3. Single-Stranded Ligation

Perform the ligation reaction according to the ligation reaction system and conditions prepared in table 28.

TABLE 28

| Compositions | Volume (μL) | Final Concentration | Ligation conditions |
|---|---|---|---|
| 10× Ligase Buffer | 4 | 1× | 60° C. |
| 50 mM MnCl$_2$ | 2 | 2.5 mM | 1 hour |
| 5M Betaine | 8 | 1 M |  |
| Thermostable RNA ligase (100 U/μL) | 2 | 5 U/μL |  |

TABLE 28-continued

| Compositions | Volume (μL) | Final Concentration | Ligation conditions |
|---|---|---|---|
| ABar-X2(200 nM) | 2 | 10 nM | |
| Extension product | 8 | | |
| 50% PEG | 14 | 17.5% | |
| Total | 40 | / | |

After ligation, the ligation product was purified by silica gel column and finally eluted with 50 μL of elution buffer.

Step 4. Amplification of the Ligation Product (Library Amplification)

According to the reaction system and conditions in table 29, PCR amplification of the ligation product was performed.

TABLE 29

| Compositions | Volume |
|---|---|
| Ligation product | 30 μL |
| 5× Q5 Buffer | 10 μL |
| dNTP (10 mM each) | 1 μL |
| Q5 high-fidelity DNA polymerase (2 U/μL) | 1 μL |
| AF (10 uM) | 1.5 μL |
| AR (10 uM) | 1.5 μL |
| ddH$_2$O | 5 μL |
| Total Volume | 50 μL |

| Temperature(° C.) | Time(s) | Cycles |
|---|---|---|
| 98 | 30 | 1 |
| 98 | 10 | 12 |
| 72 | 30 | |
| 72 | 300 | 1 |

Purify the amplified product with 80 μL of Agencourt AMPure magnetic beads, and dissolve the purified product in 30 μL, of elution buffer. At this point, the library preparation for sequencing is completed.

Step 5. Sequencing and Data Analysis

Sequencing the prepared library using an Ion Proton system. The related operations included water-in-oil PCR, library enrichment, biochip loading, and sequencing. The detailed procedure is described in the instruction manuals of Ion PITM Hi-QTM OT2 200 kit and Ion PITM Hi-QTM Sequencing 200 kit.

The analysis of sequencing results are shown in table 30 and table 31, respectively.

TABLE 30

Sequencing results 1

| Type of sample | Total reads (M) | Reads from the target region (M) | Total alignment rate | Total specificity of the reads from the target region |
|---|---|---|---|---|
| Blank (QC) | 1.261 | 0.448 | 74.35% | 47.84% |
| 5% mixed | 1.376 | 0.491 | 79.78% | 44.74% |
| 10% mixed | 1.508 | 0.513 | 75.42% | 45.10% |

TABLE 31

Results of methylation levels of each gene under different mixing ratios of DNA from intestinal cancer tissues

| Name of genes | Methylation sites on genes | Blank | 5% mixed | 10% mixed |
|---|---|---|---|---|
| SEPT9 | chr17: 75369623 | 1.89% | 4.03% | 5.82% |
| | chr17: 75369630 | 1.52% | 5.04% | 6.18% |
| | chr17: 75369657 | 1.35% | 4.97% | 5.55% |
| | chr17: 75369663 | 0.65% | 3.67% | 5.50% |
| BMF3 | chr4: 81952061 | 3.01% | 3.10% | 6.63% |
| | chr4: 81952065 | 3.72% | 4.22% | 6.86% |
| | chr4: 81952078 | 2.48% | 2.69% | 5.99% |
| | chr4: 81952099 | 2.72% | 3.57% | 5.67% |
| NDRG4 | chr16: 58497230 | 1.66% | 2.92% | 4.74% |
| | chr16: 58497236 | 1.41% | 3.69% | 4.19% |
| | chr16: 58494239 | 1.43% | 3.00% | 4.67% |
| | chr16: 58497251 | 3.17% | 5.81% | 5.89% |
| | chr16: 58497265 | 3.15% | 5.88% | 6.48% |

It can be seen from tables 30 and 31, the samples with 5% and 10% intestinal cancer tissue DNA mixed were significantly different from the blank samples in the degree of methylation. The degree of methylation of the samples with 10% intestinal cancer tissue DNA mixed is highest, the blank sample had the lowest methylation level, which was same with expectations. The results show that, the target region of DNA fragmented samples treated with bisulfite can also be well enriched and can be applied to the analysis of degree of gene methylation and related diseases by using the enrichment method of the present invention.

Example 3

The oligonucleotide sequences used in examples 3 and 4 are shown in table 32:

TABLE 32

| Name | SEQ ID NO. | Sequence (5'→3') |
|---|---|---|
| F-SRY | 20 | TTCCAGGAGGCACAGAAATTAC |
| R-SRY | 21 | CTTCCGACGAGGTCGATACT |
| MGB-SRY | 22 | CATGCACAGAGAGAAATACCCGAAT |
| F858 | 23 | CAGATTTTGGGCG |
| ER1 | 13 | TTTGCCTCCTTCTGC |
| EM1 | 14 | AACTGCTGGGTGCGGA |
| F787 | 24 | GCGTGATGAGT |
| R787 | 25 | GCGTGGACAACCCCCAC |
| MGB787 | 26 | CACGGTGGAGGTGAGGC |
| Uni-R | 27 | CCATCTCATCCCTGCGT |
| Uni-MGB | 28 | TCCGACTCAGTAAGGAGAACGA |
| Probe 8 | 29 | CCGCTTTCCTCTCTATGGGCAGTC GGGATCCAATATTGTCTTTGTGTT CCCGGACATAGTCCT-C3 Spacer |
| Probe 9 | 30 | CCGCTTTCCTCTCTATGGGCAGTC GGTGATCTATGGCCATTCTTCCAG GAGGCACAGAAATTACT-C3 Spacer |

TABLE 32-continued

| Name | SEQ ID NO. | Sequence (5'→3') |
|---|---|---|
| ABar-X2 | 10 | PO4-GGATCCNNNNNNGTTCTCCT TACTGAGTCGGAGACACGCAGGG ATGAGATGG-C3 Spacer |

Main Reagents and Materials:

Same as in Example 1, the calibrator used in qPCR was prepared according to the conventional method of molecular cloning.

Step 1. Sample Preparation

The non-small cell lung cancer cell line NCI-H1975 contains both the mutation of EGFR L858R site and the SNP of Q787 site. Genomic DNA of non-small cell lung cancer cell line NCI-H1975 and normal human leukocytes was extracted using XX kit. The genomic DNA is broken by ultrasound to the molecular weight range of 100-300 bp. After quantification by the Qubit fluorescence quantifier, the genomic DNA of NCI-H1975 was mixed into the genomic DNA of normal human leukocytes at a ratio of 1%, 0.1%, 0.03%, 0.01%, 0%, and captured-extension, ligation and library expansion were applied to the samples by step 2 to step 6 in example 1 of the present invention.

Step 2. qPCR Detection of Different Specific Primer/Probe Combinations

The trispecific, bispecific and monospecific detection systems for the EGFR gene L858R site are shown in tables 33-35.

TABLE 33

Trispecific detection system for L858R site

| Reagents | Dosage (μL) | Final concentration |
|---|---|---|
| 2× Taqman Mix | 10 | 1× |
| F858(10 μM) | 0.6 | 300 nM |
| R858(10 μM) | 0.6 | 300 nM |
| 858(10) | 0.2 | 100 nM |
| H₂O | 6.6 | / |
| Calibrator or sample to be tested | 2 | / |
| Total | 20 | / |

TABLE 34

Bispecific detection system for L858R site

| Reagents | Dosage (μL) | Final concentration |
|---|---|---|
| 2× Taqman Mix | 10 | 1× |
| F858(10 μM) | 0.6 | 300 nM |
| Uni-R(10 μM) | 0.6 | 300 nM |
| MGB858(10 μM) | 0.2 | 100 nM |
| H₂O | 6.6 | / |
| Calibrator or sample to be tested | 2 | / |
| Total | 20 | / |

TABLE 35

Monospecific detection system for L858R site

| Reagents | Dosage (μL) | Final concentration |
|---|---|---|
| 2× Taqman Mix | 10 | 1× |
| F858(10 μM) | 0.6 | 300 nM |
| Uni-R(10 μM) | 0.6 | 300 nM |
| Uni-MGB(10 μM) | 0.2 | 100 nM |
| H₂O | 6.6 | / |
| Calibrator or sample to be tested | 2 | / |
| Total | 20 | / |

The trispecific, bispecific, and monospecific detection systems for EGFR gene Q787Q site are shown in tables 36-38.

TABLE 36

Trispecific detection system for Q787Q site:

| Reagents | Dosage (μL) | Final concentration |
|---|---|---|
| 2× Taqman Mix | 10 | 1× |
| F787(10 μM) | 0.6 | 300 nM |
| R787(10 μM) | 0.6 | 300 nM |
| MGB787(10 μM) | 0.2 | 100 nM |
| H₂O | 6.6 | / |
| Calibrator or sample to be tested | 2 | / |
| Total | 20 | / |

TABLE 37

Bispecific detection system for Q787Q site:

| Reagents | Dosage (μL) | Final concentration |
|---|---|---|
| 2× Taqman Mix | 10 | 1× |
| F787(10 μM) | 0.6 | 300 nM |
| Uni-R(10 μM) | 0.6 | 300 nM |
| MGB787(10 μM) | 0.2 | 100 nM |
| H₂O | 6.6 | / |
| Calibrator or sample to be tested | 2 | / |
| Total | 20 | / |

TABLE 38

Monospecific detection system for Q787Q site:

| Reagents | Dosage (μL) | Final concentration |
|---|---|---|
| 2× Taqman Mix | 10 | 1× |
| F787(10 μM) | 0.6 | 300 nM |
| Uni-R(10 μM) | 0.6 | 300 nM |
| Uni-MGB(10 μM) | 0.2 | 100 nM |
| H₂O | 6.6 | / |
| Calibrator or sample to be tested | 2 | / |
| Total | 20 | / | qPCR detection procedures are shown in table 39.

TABLE 39

| Cycle | Temperature | Time |
|---|---|---|
| 1 cycle | 95° C. | 4 min |
| 40 cycles | 95° C. | 10 s |
|  | 61° C. | 30 s |

Experimental Results and Analysis

Results 1. The detection results of L858R sites with different specific primer/probe combinations are shown in tables 40-42, respectively. Among them, the trispecific, bispecific and monospecific detection systems respectively correspond to the reaction systems in tables 33-35.

TABLE 40

Results of trispecific detection of L858R site ($\Delta CT = ABS(mean\ Q_i-Q_5)$)

| Mixing rate | CT1 | CT2 | CT Mean | ΔCT |
|---|---|---|---|---|
| 1% | 26.13 | 26.49 | 26.31 | 11.715 |
| 0.1% | 30.35 | 30.56 | 30.46 | 7.570 |
| 0.03% | 33.43 | 33.85 | 33.64 | 4.385 |
| 0.01% | 37.34 | 36.52 | 36.93 | 1.095 |
| 0 | 38.52 | 37.53 | 38.03 | 0 |

TABLE 41

Results of bispecific detection of L858R site

| Mixing rate | CT1 | CT2 | CT Mean | ΔCT |
|---|---|---|---|---|
| 1% | 24.12 | 24.14 | 24.13 | 13.040 |
| 0.1% | 28.73 | 28.24 | 28.49 | 8.685 |
| 0.03% | 30.82 | 31.32 | 31.07 | 6.100 |
| 0.01% | 33.43 | 34.18 | 33.81 | 3.365 |
| 0 | 37.32 | 37.02 | 37.17 | 0 |

TABLE 42

Results of monospecific detection of L858R site

| Mixing rate | CT1 | CT2 | CT Mean | ΔCT |
|---|---|---|---|---|
| 1% | 23.64 | 23.52 | 23.58 | 12.850 |
| 0.1% | 27.38 | 27.02 | 27.20 | 9.230 |
| 0.03% | 29.24 | 29.87 | 29.56 | 6.875 |
| 0.01% | 32.29 | 31.58 | 31.94 | 4.495 |
| 0 | 36.24 | 36.62 | 36.43 | 0 |

Results 2. The detection results of Q787Q sites with different specific primer/probe combinations are shown in tables 43-45 respectively. Among them, the trispecific, bispecific and monospecific detection systems respectively correspond to the reaction systems in tables 36-38.

TABLE 43

Trispecific test results of Q787Q site

| Mixing rate | CT1 | CT2 | CT Mean | ΔCT |
|---|---|---|---|---|
| 1% | 26.09 | 25.85 | 25.97 | 11.055 |
| 0.1% | 30.52 | 30.82 | 30.67 | 6.355 |
| 0.03% | 34.07 | 33.59 | 33.83 | 3.195 |
| 0.01% | 36.82 | 36.43 | 36.63 | 0.400 |
| 0 | 37.14 | 36.91 | 37.03 | 0 |

TABLE 44

Bispecific detection results of Q787Q site

| Mixing rate | CT1 | CT2 | CT Mean | ΔCT |
|---|---|---|---|---|
| 1% | 25.45 | 25.48 | 25.47 | 10.820 |
| 0.1% | 29.01 | 29.48 | 29.25 | 7.040 |
| 0.03% | 31.77 | 32.11 | 31.94 | 4.345 |
| 0.01% | 34.12 | 34.98 | 34.55 | 1.735 |
| 0 | 36.05 | 36.52 | 36.29 | 0 |

TABLE 45

Monospecific detection results of Q787Q site

| Mixing rate | CT1 | CT2 | CT Mean | ΔCT |
|---|---|---|---|---|
| 1% | 24.44 | 24.17 | 24.31 | 11.950 |
| 0.1% | 27.84 | 28.19 | 28.02 | 8.240 |
| 0.03% | 30.45 | 31.01 | 30.73 | 5.525 |
| 0.01% | 32.98 | 32.45 | 32.72 | 3.540 |
| 0 | 36.03 | 36.48 | 36.26 | 0 |

Conclusion: For reference products with different mixing rates, bispecific and monospecific primer/probe systems have a larger ΔCT value and a higher effective resolution than trispecific system. when ΔCT=3 is used as cut off, for the L858R site, the detection limits of the monospecific system, bispecific system and trispecific system are 0.01%, 0.01% and 0.03% respectively; for Q787 site, the detection limits are 0.01%, 0.03% and 0.01%, respectively. This shows that the monospecific system and the bispecific system still have a reliable detection rate even the mixing rate is as low as 0.03%.

Example 4

The oligonucleotide sequences used in this example are shown in table 32.

Main reagents and materials: same as example 3.

Step 1. Sample Preparation

Extract plasma free DNA of male and female respectively by plasma free nucleic acid extraction kit. After quantification with Qubit fluorescence quantifier, at the ratio of 1%, 0.1%, 0.03%, 0.01%, 0%, mix male cfDNA into the female cfDNA sample, while using the female cfDNA as a blank control. Perform steps 2-6 in example 1 of the present invention to apply captured-extension, ligation and library expansion to the sample.

Step 2. qPCR Detection of Different Specific Primer/Probe Combinations

Trispecific, bispecific, and monospecific detection systems for specific SRY gene of male are shown in tables 46-48.

TABLE 46

Trispecific detection system for male specific SRY gene:

| Reagent | Dosage (μL) | Final concentration |
|---|---|---|
| 2× Taqman Mix | 10 | 1× |
| F-SRY(10 μM) | 0.6 | 300 nM |
| R-SRY(10 μM) | 0.6 | 300 nM |
| MGB-SRY(10 μM) | 0.2 | 100 nM |
| H₂O | 6.6 | / |
| Calibrator or sample to be tested | 2 | / |
| Total | 20 | / |

TABLE 47

Bispecific detection system for male specific SRY gene:

| Reagent | Dosage (µL) | Final concentration |
|---|---|---|
| 2 × Taqman Mix | 10 | 1× |
| F-SRY(10 µM) | 0.6 | 300 nM |
| Uni-R(10 µM) | 0.6 | 300 nM |
| MGB-SRY(10 µM) | 0.2 | 100 nM |
| H$_2$O | 6.6 | / |
| Calibrator or sample to be tested | 2 | / |
| Total | 20 | / |

TABLE 48

Monospecific detection system for male specific SRY gene:

| Reagent | Dosage (µL) | Final concentration |
|---|---|---|
| 2 × Taqman Mix | 10 | 1× |
| F-SRY(10 µM) | 0.6 | 300 nM |
| Uni-R(10 µM) | 0.6 | 300 nM |
| Uni-MGB (10 µM) | 0.2 | 100 nM |
| H$_2$O | 6.6 | / |
| Calibrator or sample to be tested | 2 | / |
| Total | 20 | / | qPCR detection procedure is shown in table 49.

TABLE 49

| Cycles | Temperature | Time |
|---|---|---|
| 1 cycle | 95° C. | 4 min |
| 40 cycles | 95° C. | 10 s |
|  | 61° C. | 30 s |

Test Results and Analysis

Results: The test results of male specific SRY genes with different specific primer/probe combinations are shown in tables 50-52 respectively. The trispecific, bispecific and monospecific detection systems correspond to the reaction systems in tables 46-48, respectively.

TABLE 50

Trispecific test results of male specific SRY gene (ΔCT = ABS(mean Qi-Q5))

| Mixing rate | CT1 | CT2 | CT mean | ΔCT |
|---|---|---|---|---|
| 1% | 31.23 | 32.08 | 31.66 | 13.345 |
| 0.1% | 35.71 | 35.94 | 35.83 | 9.175 |
| 0.03% | 37.85 | 38.02 | 37.94 | 7.065 |
| 0.01% | 39.25 | 39.52 | 39.39 | 5.615 |
| 0 | ND | ND | 45.00 | 0 |

TABLE 51

Bispecific test results of male specific SRY gene

| Mixing rate | CT1 | CT2 | CT mean | ΔCT |
|---|---|---|---|---|
| 1% | 30.55 | 30.99 | 30.77 | 14.230 |
| 0.1% | 34.23 | 34.98 | 34.61 | 10.395 |
| 0.03% | 36.32 | 37.94 | 37.13 | 7.870 |
| 0.01% | 39.48 | 39.12 | 39.30 | 5.700 |
| 0 | ND | ND | 45.00 | 0 |

TABLE 52

Monospecific test results of male specific SRY gene

| Mixing rate | CT1 | CT2 | CT mean | ΔCT |
|---|---|---|---|---|
| 1% | 29.38 | 29.68 | 29.53 | 15.470 |
| 0.1% | 33.28 | 33.89 | 33.59 | 11.415 |
| 0.03% | 35.45 | 35.82 | 35.64 | 9.365 |
| 0.01% | 38.21 | 37.89 | 38.05 | 6.950 |
| 0 | ND | ND | 45.00 | 0 |

Conclusion: As a gene only on the Y chromosome, SRY has high detection sensitivity by the three methods. If ΔCT=3 is used as the cut off, the monospecific, bispecific, and trispecific systems each can achieve a detection sensitivity of 0.01%. However, judging from the specific CT value, the detection rate of the monospecific system is higher.

In summary, the present invention effectively overcomes various shortcomings in the prior art and has high industrial utilization value.

The above embodiments are only illustrative of the principles and effects of the present invention, not intended to limit the present invention. Anyone familiar with this technology can modify or change the above embodiments without departing from the spirit and scope of the present invention. Therefore, all equivalent modifications or changes made by those with common knowledge in the technical field without departing from the spirit and technical idea disclosed by the present invention should still be covered by the claims of the present invention.

What is claimed is:

1. A kit for enriching target regions of fragmented DNA, comprising one or more specific probes, an adapter DNA, thermostable RNA ligase, dNTP coupled with biotin, and a DNA polymerase suitable for enriching a target region of a gene, wherein, a specific probe comprises a sequence complementary to the target region of the fragmented DNA, a hydroxyl group at the 3' terminal nucleotide of the specific probe is substituted with a C3 spacer, the DNA polymerase is a high-fidelity DNA polymerase with 3'-5' exonuclease activity;

a forward primer and a reverse primer, the forward primer and the reverse primer comprising sequence that is at least partially complementary to a universal sequence of the specific probe and a universal sequence of the adapter DNA; and a detection primer 1 and detection primer 2, at least one of which contains gene-specific sequence, wherein, the specific probe has a sequence of SEQ ID NO: 7.

* * * * *